(12) United States Patent
Kittur

(10) Patent No.: US 8,707,795 B2
(45) Date of Patent: Apr. 29, 2014

(54) METHOD FOR MEASURING FATIGUE

(75) Inventor: Madan Kittur, Huntington, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 57 days.

(21) Appl. No.: 13/474,250

(22) Filed: May 17, 2012

(65) Prior Publication Data

US 2013/0305833 A1 Nov. 21, 2013

(51) Int. Cl.
*G01L 1/00* (2006.01)
(52) U.S. Cl.
USPC .............................................. 73/774
(58) Field of Classification Search
USPC .............................................. 73/774
See application file for complete search history.

(56) References Cited

U.S. PATENT DOCUMENTS

| | | | | | |
|---|---|---|---|---|---|
| 2,830,286 | A | * | 4/1958 | Brunges, Jr. | 324/174 |
| 3,272,003 | A | * | 9/1966 | Harting | 73/775 |
| 3,779,071 | A | * | 12/1973 | Thomas et al. | 73/767 |
| 5,195,046 | A | * | 3/1993 | Gerardi et al. | 702/35 |
| 5,969,260 | A | * | 10/1999 | Belk et al. | 73/773 |
| 6,026,691 | A | * | 2/2000 | Laird et al. | 73/808 |
| 6,912,913 | B2 | * | 7/2005 | Murakami | 73/808 |
| 7,516,674 | B1 | * | 4/2009 | Feger et al. | 73/799 |
| 7,621,190 | B2 | * | 11/2009 | Ahmad et al. | 73/862.474 |
| 7,950,289 | B2 | * | 5/2011 | Foote | 73/786 |
| 8,510,061 | B2 | * | 8/2013 | Grant et al. | 702/38 |

OTHER PUBLICATIONS

Merchant, et al., Damage in Copper Foil Based Flexible Circuit during Mechanical Fatigue, IPC National Conference on Flex Circuits, Mar. 18, 1998, Retrieved from the Internet http://www.gould.com/e4/e139/e197/tpyear198/todownload252/DAMAGE_eng.PDF [retrieved on May 9, 2009] the whole document.
Merchant, et al, Mechanical Fatigue of Thin Copper Foil, Journal of Electronic Materials, 998-1007, vol. 28, No. 9, Jun. 1, 1999, Retrieved from the Internet: http://www.gould.com/e8/e603/e604/tpyear613/tpdownload617/MECHAN_eng.PDF [retrieved on May 5, 2012] the whole document.

* cited by examiner

*Primary Examiner* — Lisa Caputo
*Assistant Examiner* — Octavia Davis-Hollington
(74) *Attorney, Agent, or Firm* — Mark O. Glut; NAWCAD

(57) ABSTRACT

A method for measuring fatigue on a metal or metal alloy structural part, which includes mounting a fatigue gage on a surface of the part, the fatigue gage being the same material as the part, applying electrical power on the gage and measuring the resistance of the fatigue gage, inspecting the fatigue gage at various time intervals by applying electric power on the gage and measuring the resistance of the fatigue gage; and analyzing the change of resistance of the fatigue gage at the various time intervals to determine fatigue on the part.

6 Claims, 3 Drawing Sheets

METHOD FOR MEASURING FATIGUE

STATEMENT OF GOVERNMENT INTEREST

The invention described herein may be manufactured and used by or for the Government of the United States of America for governmental purposes without payment of any royalties thereon or therefor.

BACKGROUND

Every metal part, no matter how well it is manufactured, contains some flaws as a result of the manufacturing process. The flaws are randomly distributed, some are on the surface and some are located internally. Flaws manifesting close to a stress concentrator (Kt) are subjected to increased stress and therefore have an increased probability of developing micro-cracks during service. These micro-cracks then subsequently join with each other to form a bigger crack. When the part is subjected to in-service loads, the crack begins to grow.

Metal fatigue has long been a problem for the aircraft industry. In the early 1950's, the first commercial jet airliner to reach production, the de Havilland DH 106 Comet, suffered several catastrophic accidents before the cause was attributed to metal fatigue. While a great deal has been learned since the 1950's about metal fatigue, and length-of-service standards have been established for parts replacement, even today the useful life of an aircraft part is not always well quantified. Indeed, in 2011, metal fatigue likely caused a five foot hole to rupture in the fuselage of a Southwest Airlines Boeing 737 resulting in an explosive decompression at 34,000 feet that necessitated an emergency landing.

The rate at which a micro-crack grows depends upon several factors that include load levels and the number of load cycles to which the material is subjected. Fatigue may be defined as the progressive and localized damage that occurs when a material is subjected to repeated load cycles. The inception of a crack is much debated in the literature and therefore there is no universal definition of crack initiation.

Figure 1:
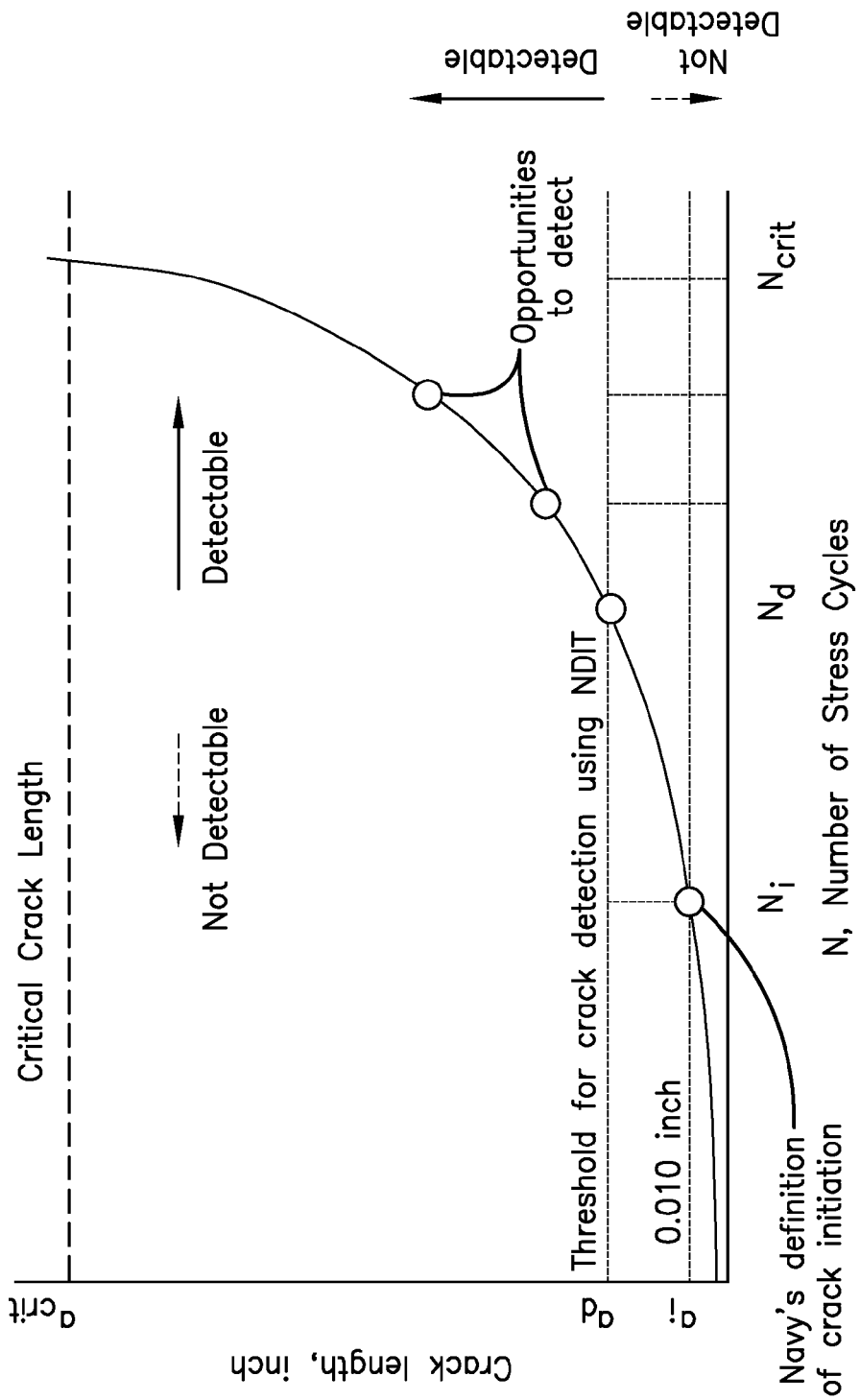

The United States Navy defines a crack to have initiated when the incipient crack reaches the length of 0.010 inch. The crack grows with applied load, eventually reaching a critical size at which point the part fails catastrophically. There are various non-destructive inspection techniques (NDITs) that allow the measurement of cracks, but only after reaching a certain size do cracks become detectable. FIG. 1 shows the general nature of crack growth, where the points on the graph: $(a_i, N_i)$, $(a_d, N_d)$, and $(a_{crit}, N_{crit})$ define crack initiation (CI), threshold of detection, and critical points, where a is the crack length and N is the number of cycles it took for the crack to reach the length of a. Inspections are generally scheduled between $N_d$ and $N_{crit}$. For some aluminum alloys subjected to a fighter aircraft spectrum, approximately two-thirds of the total life is spent in the CI phase. The crack remains undetectable for some more time from $N_i$ to $N_d$. The crack growth period from initiation in some high strength steel alloys is even shorter than aluminum, making it difficult to employ available NDITs. Thus there is a need to develop ways to detect cracks between $N_i$ and $N_d$.

Crack initiation for a given stress is determined by laboratory testing of several dog-bone-shaped coupons (a coupon is a sample of a metal or metalwork) made from the metal or alloy in question. The coupons are subjected to a constant amplitude stress cycle with a minimum stress of 0.1 of the maximum stress for the metal to be tested (ratio (R) of 0.1). These tests are repeated for different stresses and different stress ratios to get a family of life curves. This method of determining CI life is referred to in the industry as "Method 1."

Compact test specimens are typically used in studying crack growth. When such specimens are subjected to stress cycles with marker cycles introduced periodically, the crack leaves a pattern that can be studied under a microscope after the tests are completed. Such fractographic examinations can help chart the crack back to its origin. Using the Navy's definition, CI life can be determined. This method of determining CI life is referred to in the industry as "Method 2." The CI lives determined by the above two methods may not match because of the lack of a physics-based definition of initiation. Also, there is some amount of uncertainty associated with CI life for a constant amplitude spectrum. Even more uncertainty is associated with CI life when the component is subjected to a variable stress spectrum due to in-service loads such as may be encountered by an F-18 while landing or maneuvering. Therefore, some amount of uncertainty is expected for any measurement technique, especially in the neighborhood of CI life and generally below the threshold of detectability of current NDIT.

SUMMARY

The present invention is directed to a method and apparatus for measuring fatigue that meets the needs enumerated above and below.

The present invention is directed to a method for measuring fatigue on a metal or metal alloy structural part, which includes mounting a fatigue gage on a surface of the part, the fatigue gage being the same material as the part, applying electrical power on the gage and measuring the resistance of the fatigue gage, inspecting the fatigue gage at various time intervals by applying electric power on the gage, measuring the resistance of the fatigue gage; and analyzing the change of resistance of the fatigue gage over time to determine fatigue on the part.

It is a feature of the present invention to provide a method that can measure fatigue and detect cracks in structural parts before the part fails.

It is a feature of the present invention to provide a method that can measure fatigue and detect cracks in structural parts significantly before what is possible using traditional non-destructive inspection techniques.

DRAWINGS

Figure 2B:
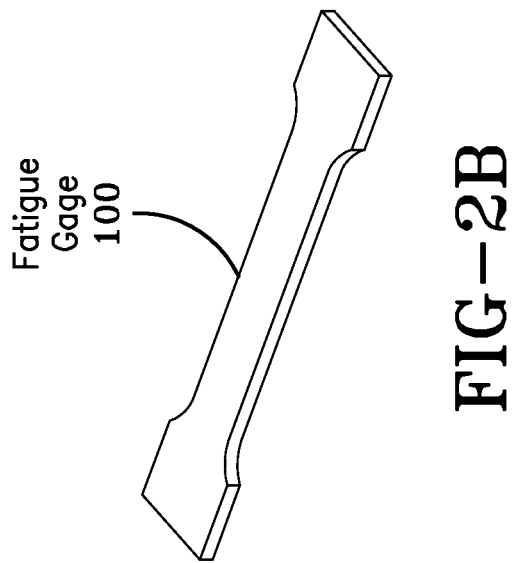
Figure 2A:
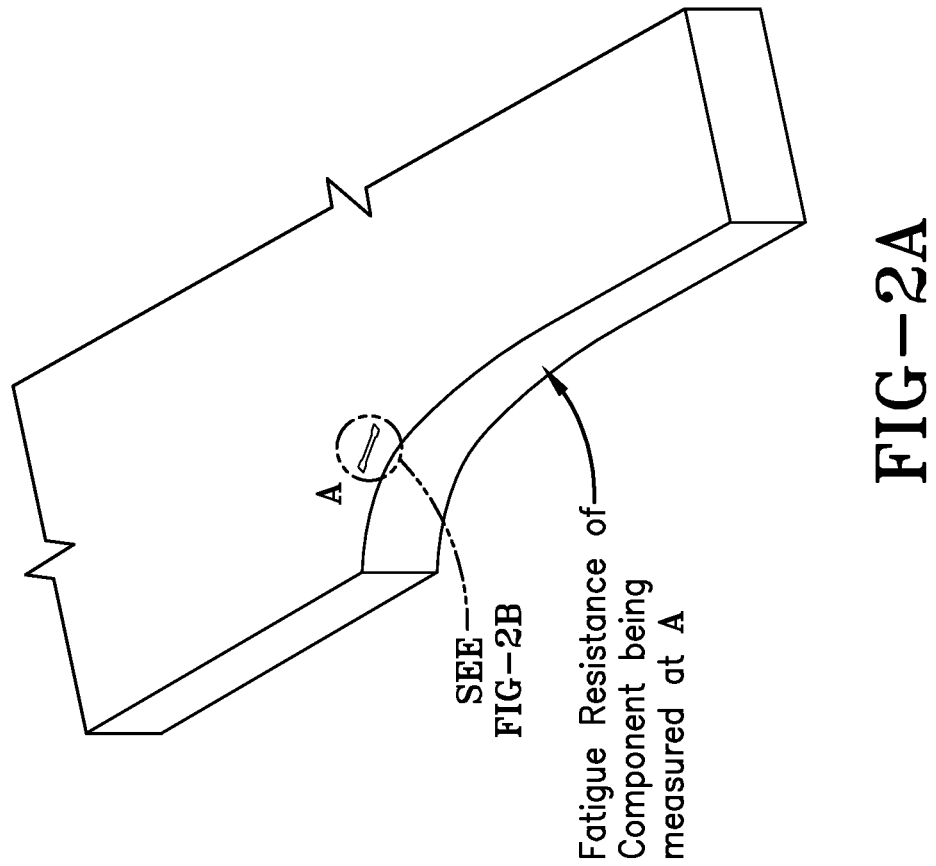
Figure 3:
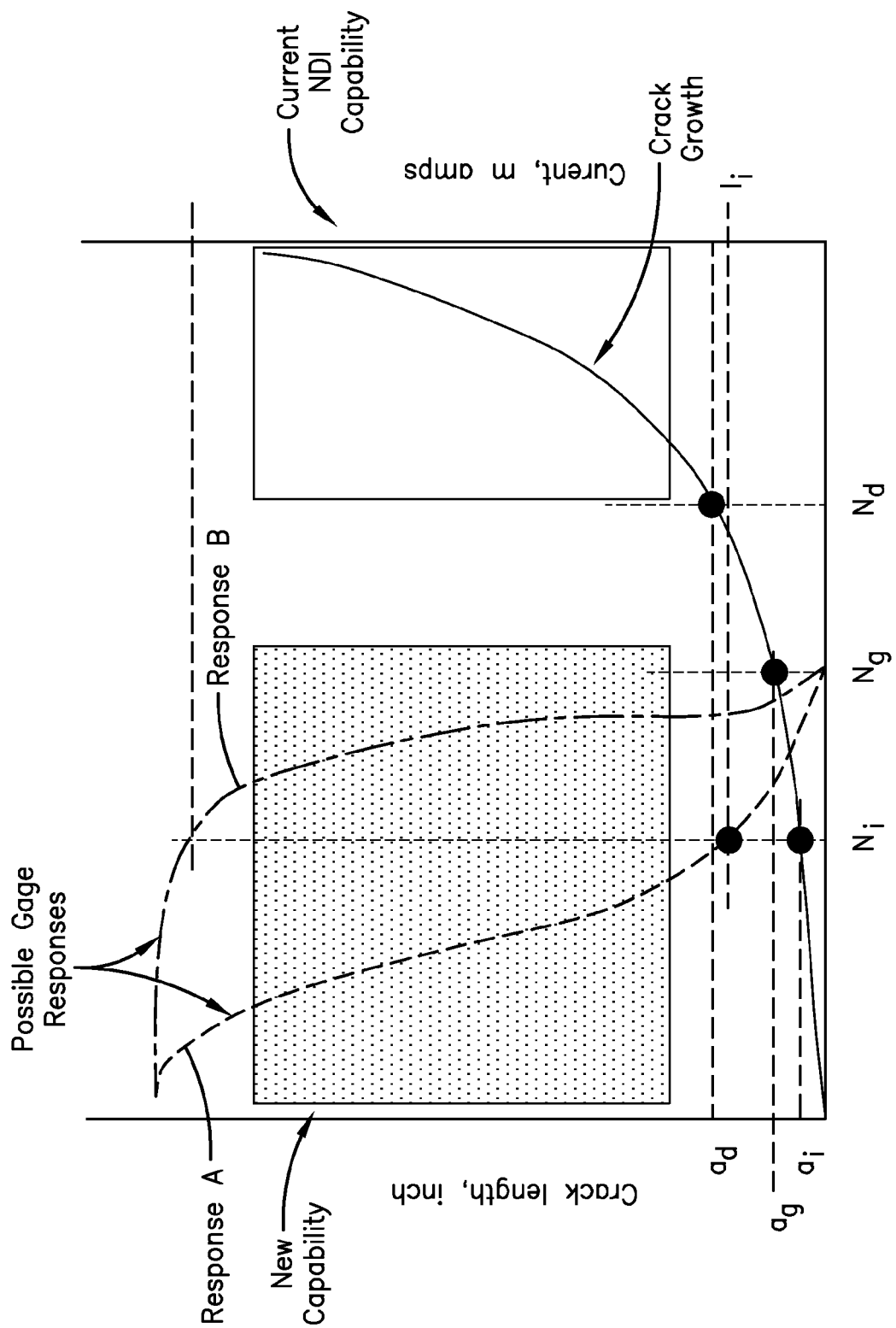

These and other features, aspects and advantages of the present invention will become better understood with reference to the following description and appended claims, and accompanying drawings wherein:

FIG. 1 is a graph depicting a typical crack growth curve;
FIG. 2A is a perspective view of the fatigue gage;
FIG. 2B is a perspective view of the fatigue gage on a part being measured; and,
FIG. 3 is a graph related to the calibration of a fatigue gage.

DESCRIPTION

The preferred embodiments of the present invention are illustrated by way of example below and in FIGS. 2-3. The method for measuring fatigue on a metal or metal alloy structural part, includes mounting a fatigue gage on a surface of the part, the fatigue gage being the same material as the part, applying electrical power on the gage and measuring the resistance of the fatigue gage, inspecting the fatigue gage at various time intervals by applying electric power on the gage and measuring the resistance of the fatigue gage; and analyzing the change of resistance of the fatigue gage at the various time intervals to determine fatigue on the part.

In the description of the present invention, the invention will be discussed in a military environment; however, this invention can be utilized for any type of application that requires use of a fatigue gage or method of determining fatigue.

As shown in FIG. 2B, the fatigue gage 100 is generally in the shape of a "dog bone" specimen as specified by American Standard Test Methods (ASTM) for testing tensile strength of a material. For example, a specimen may be ⅛ inch thick with a ¾ inch width on both ends and a ½ inch width in the middle. Since the specimen looks like a "dog bone," this term is used to refer to them. The specific geometry and dimensions of the fatigue gage 100 will depend on the application, i.e., a material of a uniform thickness and is made of the same alloy on which it is used to measure fatigue. As shown in FIG. 2B, the fatigue gage 100 is affixed directly to the surface of a metal or metal alloy component to be measured by means of an adhesive. The adhesive may be, but without limitation, an epoxy, silicone, polyurethane, or polysulfide. The adhesive is preferably coated on to one side of the gage 100 and is covered with a non-stick removable backing such as a foil or Teflon®. Because the gage 100 experiences all the stresses of the component under measurement, it is as if the coupon test is being carried out in-situ. In other words, the gage 100 may be described as a witness specimen. During the mounting of the gage 100, the backing is peeled off and the gage 100 is installed or mounted directly onto the surface of the component under measurement (the structural part being tested).

Typically the gage 100 is mounted or installed close to the point of interest as shown in FIG. 2B. As a crack is initiated in a gage 100 and it begins to grow, the cross sectional area of the gage 100 reduces. This reduction in area consequently increases the electric resistance of the gage 100. The gage 100 may be connected to a controller that continuously or periodically measures and records resistance values of one or more fatigue gages. In an alternative embodiment, fatigue gages 100 may be equipped with a wireless transmitter that provides resistance values to a remote receiver. In a further alternative embodiment, gages may be equipped with a Radio Frequency Identification transponder circuit that may be interrogated for resistance values.

An electric current is required only during inspection. A measuring-inspecting unit may supply the electric current and measure the resistance of the gage 100. In one of the embodiments, the measuring-inspecting unit supplies the 3 arms of a Wheatstone bridge while the 4th arm is the fatigue gage. When the gage 100 fails completely, there will be no current carried in the gage 100, and the structural part is in danger of failing due to fatigue. Fatigue gages could be designed to resist constant amplitude fatigue cycles at stresses, such as 20 ksi, 30 ksi, 40 ksi, and so on, and tested to fail in the laboratory at $10^4$ $10^5$, and $10^6$ cycles, for example. The gage shown in FIG. 2B is a smooth dog-bone specimen. Gages can also be designed to have stress concentrators or notches.

To calibrate a fatigue gage, a fatigue gage is mounted on the fatigue test specimen with a known stress concentration factor (Kt). A stress concentration factor is the ratio of the maximum stress in the region of a stress concentrator (notch) to the stress in a similarly strained area without a stress concentrator. The fatigue specimen is subjected to constant amplitude stress cycles with known R ratio (minimum stress/maximum stress) along with marker cycles introduced periodically. The gage is continuously monitored and recorded for the change in resistance or the electric current it is carrying as the specimen is tested. The number of fatigue cycles it takes for the gage to fail completely ($N_g$) is recorded as well. After the specimen fails, the fatigue test is continued for some more time to ensure that a crack has indeed formed for the explicit reason that there is uncertainty associated with initiation. The fatigue test is stopped by choice or when the test specimen has failed completely. If the specimen has not failed completely, it is broken open and the fractured surface is analyzed using Fractography. Marker cycles embedded in the spectrum will allow for plotting the crack growth curve as shown in FIG. 3. The number of cycles it took for crack initiation, $N_i$, can be identified on the crack growth curve shown in FIG. 3 where it passes the length of 0.010 inch. The threshold of detectability of current NDI techniques, ($a_d$, $N_d$) is also shown for reference. Since $N_g$ is recorded, the corresponding crack length, $a_g$ can be identified. If multiple experiments repeatedly provide consistent results, then the fatigue gage can be said to detect a crack size smaller than the previous threshold. Since the current carried by the gage is continuously recorded, its variation with load cycles can be plotted as shown in FIG. 3. Assuming that the response is shown in FIG. 3 by the curve identified as Response A, it is possible to determine the current carried in the gage when the crack reaches 0.010 inch. In fact, this curve (Response A) allows for detecting crack sizes smaller than 0.010 inch by measuring the current carried. However, if the response is more like the curve identified as Response B, then it may be difficult to get to the 0.010 inch as there is very small drop in the current carried. The curve shown in Response B will have a higher uncertainty in determining the crack length. A family of curves can be constructed after performing fatigue tests with gages of different $Kt_g$ values. These curves will help in selecting the best gage for each particular need.

Using these fatigue gages as in-situ test specimens will help determine the equivalent fatigue damage in terms of constant amplitude and fixed R ratio. If these gages are placed on all aircraft at the same critical location, then the relative severity of one set of aircraft assigned one set of missions can be compared with those of the aircraft in other mission assignments. If the most damaging mission can be isolated, then aircraft can be managed by modifying the mission to be less damaging or spreading the most damaging mission to all aircraft. The data obtained from these gages will directly help in ranking the criticality of each hotspot. Fractographic examinations of the top few critical spots will help to reconfirm the results read from the fatigue gages. These gages will help in determining when to schedule repairs of the critical locations that have shown to be cracked significantly before what is possible using traditional NDITs.

Components that are subjected to dynamic loading (such as in a rotor assembly or components such as flaps and ailerons) are difficult to manage because of the difficulty in determining the exact load spectrum. However, fatigue gages will solve the problem as they act as witness test specimens. High cycle fatigue is another place where fatigue gages will be very helpful. Typical stress-life curve is flat in the high cycle region. Also in this region surface defects stop ruling the failures and allow sub-surface defects to act as seeds for cracking. Experiments using fatigue gage with simulated sub-surface flaws will help in managing high cycle fatigue.

When introducing elements of the present invention or the preferred embodiment(s) thereof, the articles "a," "an," "the," and "said" are intended to mean there are one or more of the elements. The terms "comprising," "including," and "having"

are intended to be inclusive and mean that there may be additional elements other than the listed elements.

Although the present invention has been described in considerable detail with reference to certain preferred embodiments thereof, other embodiments are possible. Therefore, the spirit and scope of the appended claims should not be limited to the description of the preferred embodiment(s) contained herein.

What is claimed is:

1. A method for measuring fatigue on a metal or metal alloy structural part, comprising:
    (a.) mounting a fatigue gage on a surface of the part, the fatigue gage being the same material as the part;
    (b.) applying electrical power on the gage and measuring the resistance of the fatigue gage;
    (c.) inspecting the fatigue gage at various time intervals by applying electric power on the gage and measuring the resistance of the fatigue gage; and
    (d.) analyzing the change of resistance of the fatigue gage at the various time intervals to determine fatigue on the part.

2. The method of claim 1, wherein the fatigue gage is dog bone shaped.

3. The method of claim 1, wherein the fatigue gage is calibrated prior to mounting.

4. The method of claim 3, wherein the fatigue gages is equipped with a Radio Frequency Identification transponder circuit which can be interrogated for resistance values.

5. The method of claim 4, wherein the fatigue gages is equipped with a wireless transmitter that provides resistance values to a remote receiver.

6. The method of claim 4, wherein the fatigue gage is calibrated by:
    mounting a test fatigue gage on a fatigue test specimen with a known stress concentration factor;
    subjecting the fatigue test specimen to constant amplitude stress cycles with a known minimum stress/maximum stress ratio, continuing until a crack forms;
    applying an electric current to the test fatigue gage;
    monitoring and recording the change in resistance the test fatigue gage; and,
    plotting a crack growth curve and a response curve to determine which type of gage should be utilized.

* * * * *